(12) United States Patent
Shapir

(10) Patent No.: US 11,484,222 B2
(45) Date of Patent: Nov. 1, 2022

(54) SINGLE INFRARED SENSOR CAPNOGRAPHY

(71) Applicant: ORIDION MEDICAL 1987 LTD, Jerusalem (IL)

(72) Inventor: Erez Shapir, Jerusalem (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 766 days.

(21) Appl. No.: 15/290,160

(22) Filed: Oct. 11, 2016

(65) Prior Publication Data
US 2017/0100058 A1 Apr. 13, 2017

Related U.S. Application Data

(60) Provisional application No. 62/239,933, filed on Oct. 11, 2015.

(51) Int. Cl.
| | |
|---|---|
| *A61B 5/08* | (2006.01) |
| *A61B 5/11* | (2006.01) |
| *A61B 5/083* | (2006.01) |
| *A61B 5/024* | (2006.01) |
| *A61B 5/00* | (2006.01) |
| *A61B 5/113* | (2006.01) |

(52) U.S. Cl.
CPC ............ *A61B 5/082* (2013.01); *A61B 5/0077* (2013.01); *A61B 5/024* (2013.01); *A61B 5/0816* (2013.01); *A61B 5/0836* (2013.01); *A61B 5/11* (2013.01); *A61B 5/1135* (2013.01); *A61B 5/1128* (2013.01); *A61B 2562/0233* (2013.01)

(58) Field of Classification Search
CPC ..... A61B 5/0205; A61B 5/082; A61B 5/0836; A61M 2230/432
See application file for complete search history.

(56) References Cited

U.S. PATENT DOCUMENTS

| | | | | | |
|---|---|---|---|---|---|
| 4,572,208 | A | * | 2/1986 | Cutler ................... | A61B 5/083 128/205.12 |
| 4,966,155 | A | * | 10/1990 | Jackson ................. | A61B 5/222 600/483 |
| 5,386,833 | A | * | 2/1995 | Uhen ................... | A61B 5/0836 73/23.3 |
| 2004/0210154 | A1 | * | 10/2004 | Kline .................... | A61B 5/417 600/532 |
| 2012/0016251 | A1 | * | 1/2012 | Zhang .................. | A61B 5/0402 600/532 |
| 2013/0245483 | A1 | * | 9/2013 | Eichler .................. | A61B 5/082 600/532 |

\* cited by examiner

*Primary Examiner* — Allen Porter
*Assistant Examiner* — Michael A Catina
(74) *Attorney, Agent, or Firm* — Cantor Colburn LLP

(57) ABSTRACT

The present disclosure presents methods, systems and devices for performing capnography (respiratory $CO_2$) monitoring using a respiratory $CO_2$ sensor and a breath tracking mechanism for tracking and/or detecting phases of the breath wherein the measurements of the $CO_2$ sensor may provide baseline $CO_2$ values, and modulate/quantify the respiratory $CO_2$ levels according to the baseline values.

14 Claims, 9 Drawing Sheets

SINGLE INFRARED SENSOR CAPNOGRAPHY

CROSS-REFERENCE TO RELATED APPLICATION

This application claims priority to U.S. Provisional Application No. 62/239,933, filed Oct. 11, 2015, and is incorporated by reference herein in its entirety.

TECHNICAL FIELD

The present disclosure generally relates to the field of capnography.

BACKGROUND

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Capnography, or generally the monitoring of respiratory $CO_2$ levels in gasses, is commonly attained by radiating electromagnetic waves at $CO_2$-containing gas mixtures and analyzing the absorption behavior of the mixture. For example, by radiating electromagnetic waves at a wavelengths of approximately 4.2 micro-meters (which is a wavelength with high absorptivity rate for $CO_2$ molecules), one may obtain a measurement of the $CO_2$ levels within the gas mixture by measuring the intensity of the radiation that passed through the mixture using a main IR sensor.

For obtaining quantifiable capnography measurements, the utilization of a second IR sensor (reference sensor) is commonly used. The reference sensor is used for generating a baseline measurement of ambient $CO_2$ levels, and the baseline measurement is then used as a reference measurement for interpreting the measurements of the active IR sensor. Additional technical steps may be performed for providing such a functionality, for example a "zeroing" step in which both the main sensor and the reference sensor measure the intensity of radiation through ambient gas, and the difference between the measurements is then compensated for accurate results. Furthermore, measuring a baseline proves to be useful in detecting and compensating for drifts in the radiation source and/or sensor(s).

The utilization of two sensors and the additional technical steps results in a high cost and complexity of capnography systems.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other advantages or improvements.

According to some embodiments, there are provided herein devices, systems and methods for measuring $CO_2$ levels in respiratory gasses by using a $CO_2$ sensor for measuring the $CO_2$ levels within a chamber, and a respiratory tracking mechanism for identifying/detecting various respiratory phases. According to some embodiments, the respiratory tracking mechanism is configured to detect baseline-phases, at which the measured $CO_2$ levels are indicative of ambient $CO_2$ levels and therefore may be used for generating a baseline.

According to some embodiments, the baseline measurements may be used for recompensing/atoning/modulating the $CO_2$ levels measured during other respiratory phases, and thereby enable providing quantifiable $CO_2$ measurements.

Advantageously, having only one $CO_2$ (IR) sensor may result in lowering the cost and complexity of capnography devices and systems, compared to current capnography systems that utilize multiple $CO_2$ (IR) sensors.

According to some embodiments, there is provided a capnography device, including a respiratory-tracking mechanism, configured to provide a tracking-signal indicative of baseline-phase(s) within respiratory cycle(s), an absorption-chamber, configured to facilitate flow of respiratory gasses therethrough, a carbon dioxide ($CO_2$) sensor, configured to provide respiratory $CO_2$ measurements of respiratory gasses within the absorption-chamber, and processing circuitry.

According to some embodiments, the processing circuitry is configured to obtain respiratory $CO_2$ measurements from the $CO_2$ sensor, detect baseline-phases from the tracking-signal, distinguish baseline $CO_2$ measurements from the respiratory $CO_2$ measurements, associated with baseline-phases, and derive $CO_2$ levels based on the baseline $CO_2$ measurements and the respiratory $CO_2$ measurements.

According to some embodiments, the processing circuitry is configured to derive the $CO_2$ levels by factoring the respiratory $CO_2$ measurements with at least some baseline $CO_2$ measurements.

According to some embodiments, the processing circuitry is configured to derive the $CO_2$ levels based on the baseline $CO_2$ measurements and the respiratory $CO_2$ measurements by establishing a baseline value from the baseline $CO_2$ measurements, and dividing the respiratory $CO_2$ measurements by the baseline value, thereby deriving respiratory $CO_2$ levels.

According to some embodiments, the respiratory-tracking mechanism is configured to obtain a signal from the carbon dioxide sensor and detect various respiratory phases based on changes in the obtained signal.

According to some embodiments, the respiratory-tracking mechanism includes a heart pulse-rate sensor.

According to some embodiments, the respiratory-tracking mechanism includes a chest displacement tracking mechanism configured to provide a signal indicative of displacement in a chest of a patient.

According to some embodiments, the chest displacement tracking mechanism includes a camera configured to obtain visual imagery indicative of chest displacement.

According to some embodiments, the visual imagery include imagery of a chest area of a subject.

According to some embodiments, the chest displacement tracking mechanism includes an accelerometer configured to measure the acceleration/movement of at least one point on the chest of the subject.

According to some embodiments, the chest displacement tracking mechanism includes at least two proximity sensors, configured to be placed at two different spots on the chest of the subject and provide chest displacement tracking by measuring the proximity therebetween.

According to some embodiments, the chest displacement tracking mechanism includes a belt configured to be placed on or wrap around a chest of a subject and provide chest displacement tracking by measuring the expansion and contraction of the chest.

According to some embodiments, there is provided a method for monitoring carbon dioxide ($CO_2$) in respiratory gasses of a subject, the method including obtaining a tracking-signal indicative of respiration-phases within respiratory cycles, identifying baseline-phases based on the tracking-signal, obtaining respiratory $CO_2$ measurements, distinguishing baseline $CO_2$ measurements from the respiratory $CO_2$ measurements, based on the identified baseline-phases, and deriving respiratory $CO_2$ levels based on the distinguished baseline measurements and respiratory $CO_2$ measurements.

According to some embodiments, deriving $CO_2$ levels based on the measured baseline measurements and the respiratory $CO_2$ measurements includes establishing a baseline value from the baseline measurements.

According to some embodiments, deriving respiratory $CO_2$ levels based on the measured baseline measurements and the respiratory $CO_2$ measurements further includes subtracting the baseline value from the respiratory $CO_2$ measurements, thereby deriving respiratory $CO_2$ levels.

According to some embodiments, obtaining a tracking-signal indicative of respiration-phases within respiratory cycles includes obtaining a tracking-signal from a respiratory-tracking mechanism.

According to some embodiments, the respiratory-tracking mechanism includes a chest displacement-tracking device.

According to some embodiments, the displacement-tracking device includes a camera configured to provide visual imagery indicative of movements of a torso of a subject.

According to some embodiments, the displacement-tracking device includes a motion sensor configured to be placed on a chest or torso of a subject and to measure movements thereof.

According to some embodiments, the displacement-tracking device includes a belt or strap configured to be placed on or around the chest or torso of a subject and to measure the expansion and contraction thereof.

According to some embodiments, baseline-phases are phases in respiratory cycles that are confined between the end of inhalation and start of exhalation, and in which the respiratory gas flow is idle.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some, or none of the enumerated advantages.

In addition to the exemplary aspects and embodiments described above, further aspects and embodiments will become apparent by reference to the figures and by study of the following detailed descriptions.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

The current capnography systems commonly utilize two distinct IR sensors, one of which is configured to measure the $CO_2$ concentration in respiratory gas of a subject, while the other IR sensor is utilized for establishing a baseline value. The CO2 level values are commonly interpreted using the reference intensity ($I_0$) that might be change due to various effects. Therefore, in order to keep a constant baseline value for reliable CO2 level measurements, a correction/calibration (such as auto-zero) is commonly done using a second reference sensor or an external breathing tracking device. The established baseline value is commonly used for calibrating the measurements of the main sensor to provide meaningful/quantifiable $CO_2$ concentration measurements in the respiratory gas.

Figure 1:
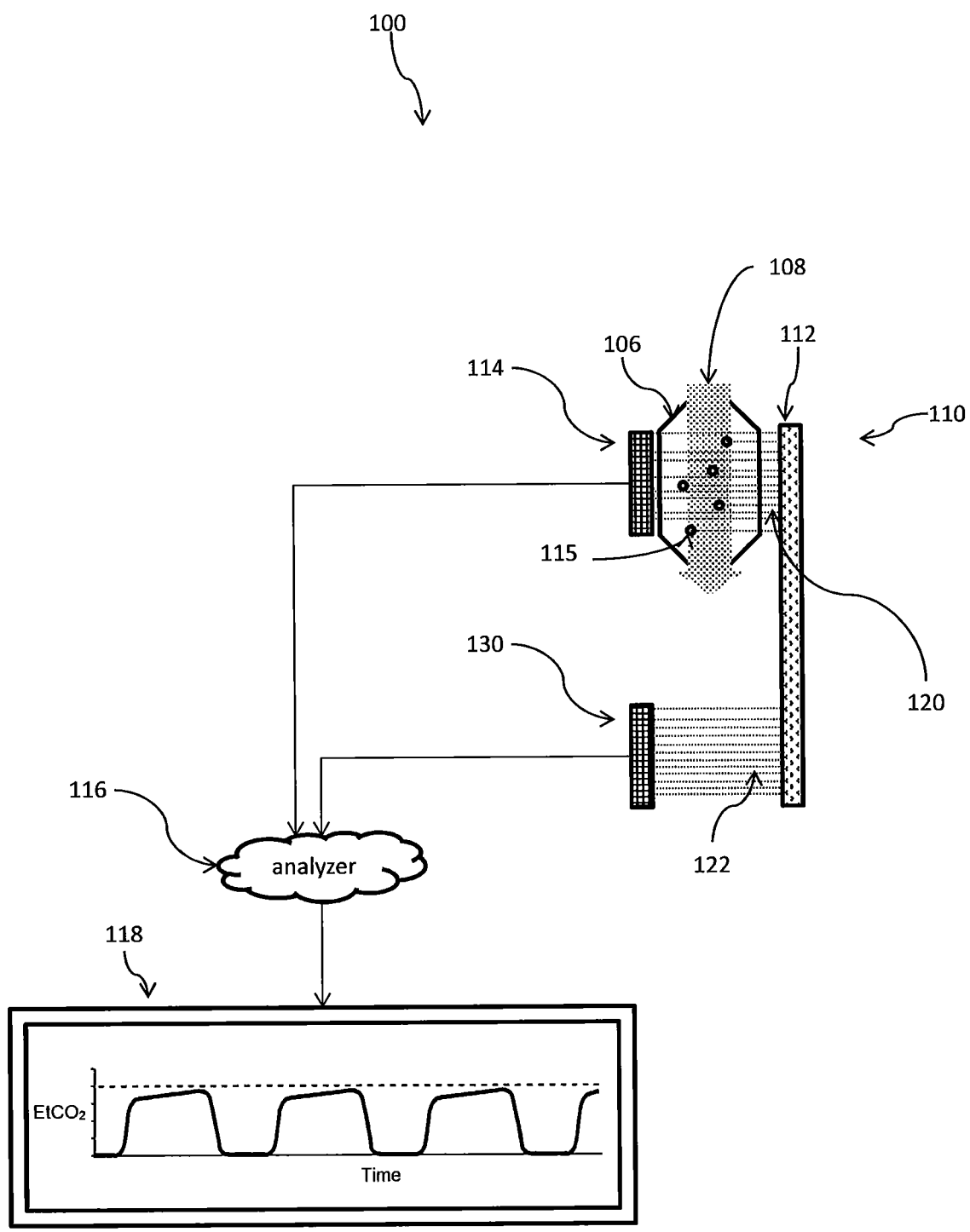
FIG. 1 schematically illustrates a common capnography system.

Reference is now made to FIG. 1, which schematically illustrates a common capnography system 100. As illustrated, capnography system 100 includes a $CO_2$ sensor 110 having an absorption chamber 106 configured to facilitate the flow of respiratory gasses 108 therethrough, an IR source 112 is commonly used to provide IR radiation 120 to absorption chamber 106, some of IR radiation 120 is absorbed by $CO_2$ molecules 115 within absorption chamber 106, and IR radiation 120 that is not absorbed reaches an IR detector, such as main-sensor 114. The amount of IR radiation 120 that reaches main-sensor 114 is indicative of the concentration of $CO_2$ molecules 115 within absorption-chamber 106. Additionally, capnography system 100 includes a reference-sensor 130, which is configured to provide an IR intensity/flux reading of radiation 122 irradiated thereto from IR source 112. The measurements of reference sensor 130 are indicative of the zero $CO_2$ concentrations in the respiration of the patient (the zero $CO_2$ concentration/level may be interchangeable with the term baseline level).

Capnography system 100 further includes an analyzer 116, configured to obtain measurements from main-sensor 114 and reference-sensor 130, and to modulate the measurements of main-sensor 114 according to the baseline measurements of reference-sensor 130. Analyzer 116 then provides $CO_2$ levels to be displayed on a monitor 118. Analyzers of this type are well-known in the art.

The need for a second IR sensor, such as reference-sensor 130, results in complicating the capnographic systems and affects the form-factor of the system as well as the cost thereof.

According to some embodiments, there are provided herein capnographic systems, devices and methods for achieving quantifiable $CO_2$ measurements using an IR sensor configured to measure respiratory $CO_2$ concentrations, and a breath/respiratory tracking mechanism for tracking respiration cycles and identifying "baseline-phases" within the respiration cycles. According to some embodiments, the $CO_2$ measurements of the IR sensor during at least some baseline-phases are indicative of $CO_2$ measurements of the respiratory zero $CO_2$ level (that may be referred to as an ambient measurements in some embodiments).

According to some embodiments, the respiratory-tracking mechanism is configured to provide a tracking-signal indicative of baseline-phases within respiratory cycles (or other phases within respiratory cycles, for example within inhalation), and the carbon dioxide ($CO_2$) IR sensor, configured to provide respiratory $CO_2$ measurements of respiratory gasses within an absorption-chamber to facilitate flow of respiratory gasses therethrough. According to some embodiments, the devices and systems may include processing circuitry, an analysis unit and/or an analyzer configured to obtain respiratory $CO_2$ measurements from the $CO_2$ sensor, detect baseline-phases from the tracking-signal, distinguish baseline $CO_2$ measurements from the respiratory $CO_2$ measurements, associated with baseline-phases, and derive $CO_2$ levels based on the baseline $CO_2$ measurements and the respiratory $CO_2$ measurements.

According to some embodiments, the term "$CO_2$ sensor" may refer to a device or unit configured to measure $CO_2$ molecule concentration in gas. According to some embodiments, a $CO_2$ sensor may include an "IR sensor" for detecting IR intensities of radiation irradiated from an IR source and passed through a $CO_2$ containing gas. The detection of high IR intensities may indicate low $CO_2$ molecule concentration within the gas, while the detection of low IR intensities may indicate high $CO_2$ molecule concentration within the gas.

According to some embodiments, the respiratory tracking mechanism is configured to track at least some respiration cycles of a user/subject, and to indicate various phases therein.

According to some embodiments, the respiratory tracking mechanism is configured to provide indication of the following phases:
Inspiration phase: the phase in which gas is inspired into the respiratory system of the subject, associated with negative gas flow (from the respiratory system outwards) and an expansion of the torso or parts thereof.
Expiration phase: the phase in which gas is expired from the respiratory system, associated with positive gas flow (from the respiratory system outwards) and a contraction of the torso or parts thereof.

According to some embodiments, the respiratory tracking mechanism is further configured to provide indication of the following intermediary phases:
Hold phase: The phase confined between by the end of the inspiration phase and the beginning of the expiration phase, associated with null gas flow (from the respiratory system outwards) and an expanded torso or parts thereof.
Vacant phase: The phase confined between by the end of the expiration phase and the beginning of the inspiration phase, associated with null gas flow (from the respiratory system outwards) and a contracted torso or parts thereof.

According to some embodiments, during a hold phase, the absorption-chamber is filled with ambient gas. According to some embodiments, the $CO_2$ measurements within the chamber during the hold phases may be representative of a respective zero-level or baseline level of $CO_2$. According to some embodiments, the terms "zero-level" and "baseline-level" are interchangeable and may refer to an ambient $CO_2$ measurement level.

According to some embodiments, the hold phases are referred to as "baseline-phases" and the $CO_2$ measurements within the chamber during the baseline-phases may be representative of ambient $CO_2$ measurements and may be utilized for establishing a baseline value for the capnography.

Figure 2:
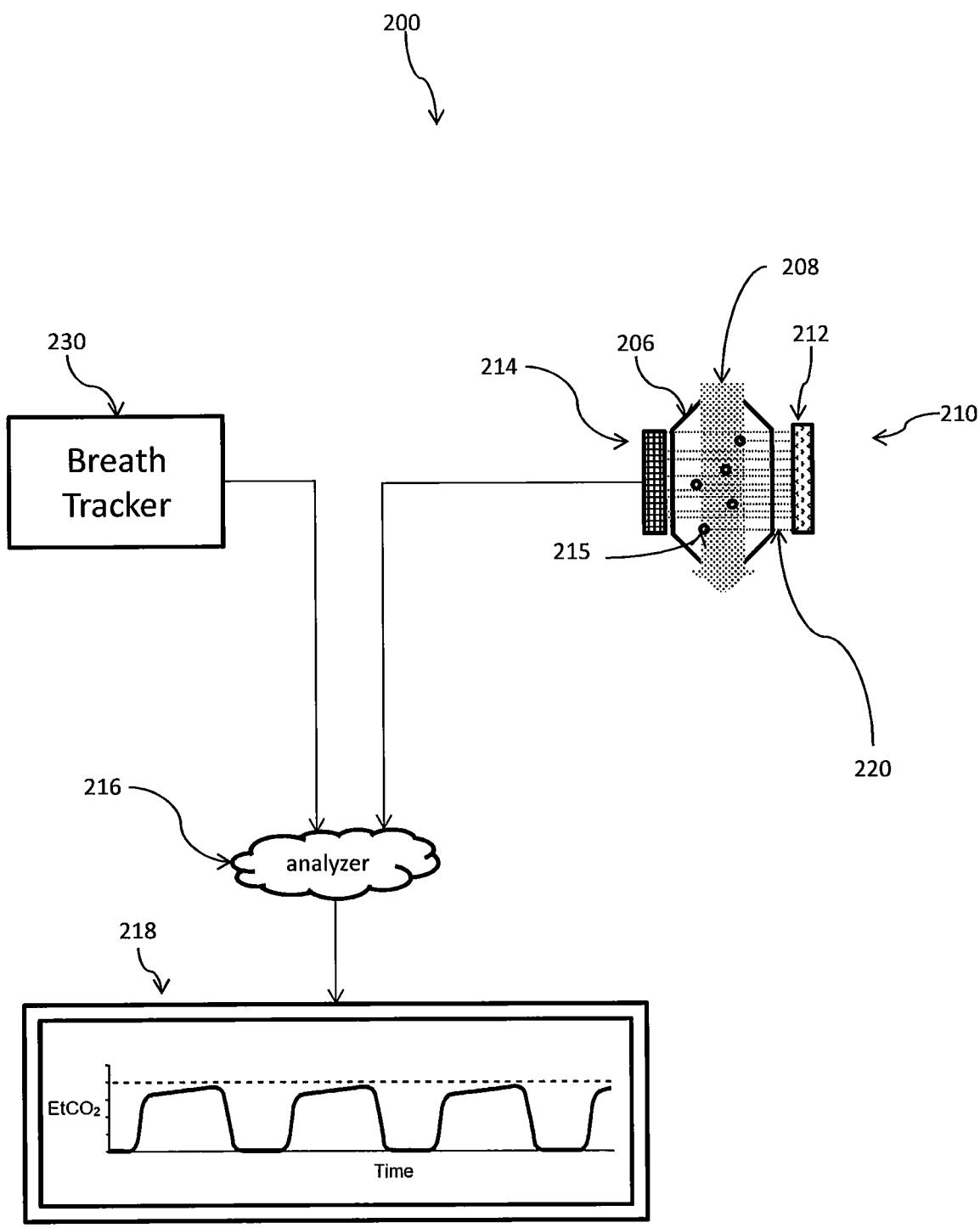
FIG. 2 schematically illustrates a capnography system with a breath tracking mechanism, according to some embodiments.

Reference is now made to FIG. 2, which schematically illustrates a capnography system 200 with a breath tracking mechanism, such as a breath tracker 230, according to some embodiments. According to some embodiments, capnography system 200 includes a $CO_2$ sensor 210 for measuring $CO_2$ molecule concentration. According to some embodiments, $CO_2$ sensor 210 includes an IR source 212 which is configured to provide IR radiation 220 through a absorption chamber 206 to an IR sensor 214. According to some embodiments, absorption chamber 206 is configured to facilitate the flow of respiratory gas 208 therethrough.

According to some embodiments, IR radiation 220 passes through respiratory gas 208 within absorption chamber 206 and at least some of radiation 220 is absorbed by $CO_2$ molecules 215 within respiratory gas 206 and the rest of radiation 220 or parts thereof then reaches IR sensor 214, which measures IR intensities. When IR sensor 214 measures high IR intensities, it may indicate low $CO_2$ molecule 215 concentrations within respiratory gas 208 in chamber 206. On the other hand, when IR sensor 214 measures low IR intensities, it may indicate low $CO_2$ molecule 215 concentration within respiratory gas 208 in chamber 206. According to some embodiments, the IR intensity measurements/readings are provided to an analyzer 216 configured to analyze the measurements and derive quantifiable $CO_2$ measurements therefrom.

According to some embodiments, breath tracker 230 is configured to track the breath/respiration cycles of a user/subject. According to some embodiments, the tracking is indicative of baseline-phases, in which gas 208 within chamber 206 is representative of ambient gas, and as a result, $CO_2$ concentration measurements during the baseline-phases may be indicative, among other factors, of a background ambient $CO_2$ concentration, and therefore provide baseline $CO_2$ measurements.

According to some embodiments, analyzer 216 is further configured to associate $CO_2$ measurements by $CO_2$ sensor 210 with respiration/breath phases. According to some embodiments, analyzer 216 is configured to identify baseline-phases and associate baseline $CO_2$ measurements to them.

According to some embodiments, analyzer 216 is further configured to establish a baseline value from the baseline $CO_2$ measurements. According to some embodiments, analyzer 216 is configured to adjust the respiratory $CO_2$ measurements based on the established baseline value and provide $CO_2$ levels to a monitor 218 for displaying the capnogram ($CO_2$ levels). The analyzer 216 may be a known analyzer (such as those available from Medtronic) reconfigured to process the information/signals from the $CO_2$ sensor 210 and the breath tracker 230 in accordance with the techniques disclosed herein.

In current capnography systems, a zeroing/calibration loop is commonly performed during capnography measurements to compensate on measurement drifts between the two sensors (the main $CO_2$ sensor and the reference $CO_2$ sensor), and for obtaining calibrated $CO_2$ measurement. Advantageously, reducing the number of sensors to only one sensor may simplify the zeroing/calibration loop by obviating the need for measuring and compensating on the drifts between the two sensors.

As used herein, the term "absorption-chamber" may refer to a cavity/chamber structure configured to facilitate a flow of respiratory gasses therein for measuring $CO_2$ levels within the gas, for example by measuring the absorption of radiated IR waves.

Advantageously, simplifying the zeroing loop (baselining) during capnography may avail the utilization of one IR sensor instead of two sensors as in common capnographic devices. As a result, the overall complexity of the capnography system is reduced and the configuration and/or maintenance thereof may be simplified.

Figure 3:
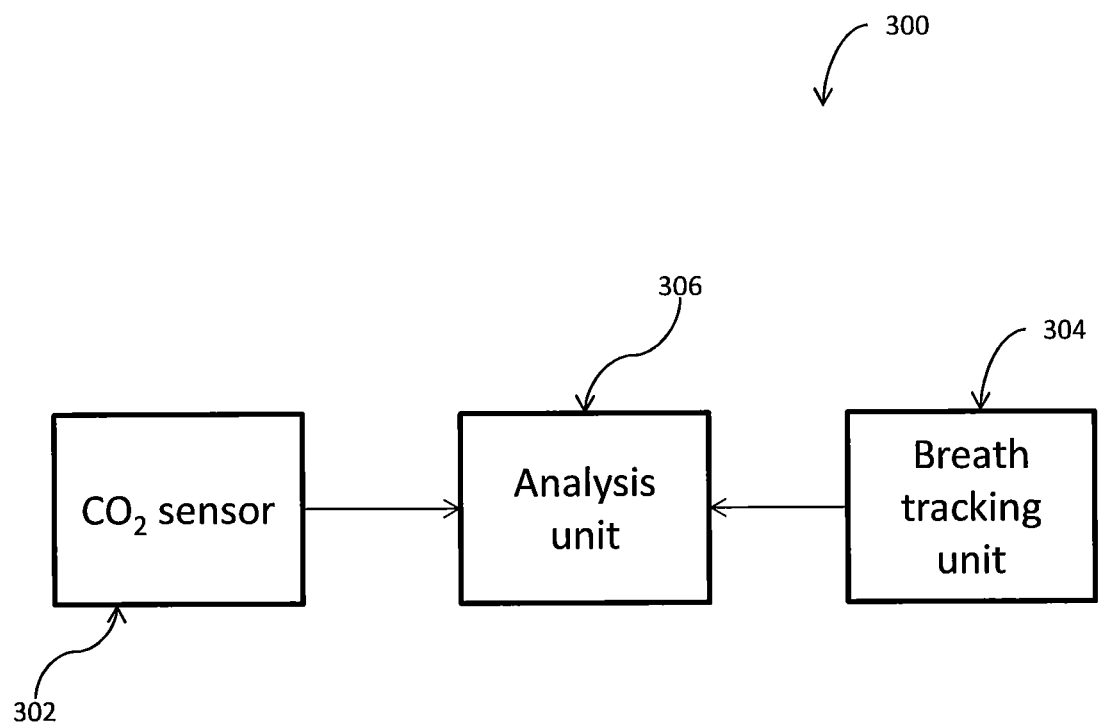
FIG. 3 schematically illustrates a block diagram of a capnography system with a breath tracking mechanism, according to some embodiments.

Reference is now made to FIG. 3, which schematically illustrates a block diagram of a capnography system 300 with a breath tracking unit 304, according to some embodiments. According to some embodiments, capnography system 300 includes an analysis unit 306 configured to obtain from breath tracking unit 304 a tracking-signal indicative of baseline-phases of respiratory cycles of a user, and to obtain respiratory $CO_2$ measurements from a $CO_2$ sensor 302.

According to some embodiments, analysis unit 306 is configured to identify baseline-phases from the tracking signal, and to associate $CO_2$ measurements with the baseline phases. According to some embodiments, the $CO_2$ measurements associated with the baseline-phases are referred to as baseline $CO_2$ measurements. According to some embodiments, analysis unit 306 is configured to establish a baseline value from the baseline $CO_2$ measurements. According to some embodiments, analysis unit 306 is configured to provide $CO_2$ levels by offsetting/altering/modifying the respiratory $CO_2$ measurements based on the established baseline value.

According to some embodiments, a breath/respiration tracking mechanism, unit or device may include tracking the expansion and contraction of the torso of a user, or parts thereof (such as the chest area). According to some embodiments, the breath/respiration tracking mechanism may include one or more accelerometers, motion sensors, proximity sensors or the like. According to some embodiments, the breath/respiration tracking mechanism may include a camera configured to obtain visual imagery of the torso area of a user, or parts thereof. According to some embodiments, the breath/respiration tracking mechanism may include one or more microphones configured to obtain audial signals associated with the breath activity of a user.

According to some embodiments, the analysis unit or analyzer may include processing circuitry configured to provide one or more of the functions associated with the analysis unit. According to some embodiments, the analysis unit may include a computer, a mobile device, a server, an FPGA system, an ASIC system or the like. According to some embodiments, the analysis unit may be connected to the $CO_2$ sensor, the breath tracking unit and/or the display wirelessly or through wired communication. According to some embodiments, the analysis unit may be connected to a local network or a wide network. According to some embodiments, the analysis unit may provide $CO_2$ levels to a distant user or location through internet/cellular/satellite communication.

Figure 4:
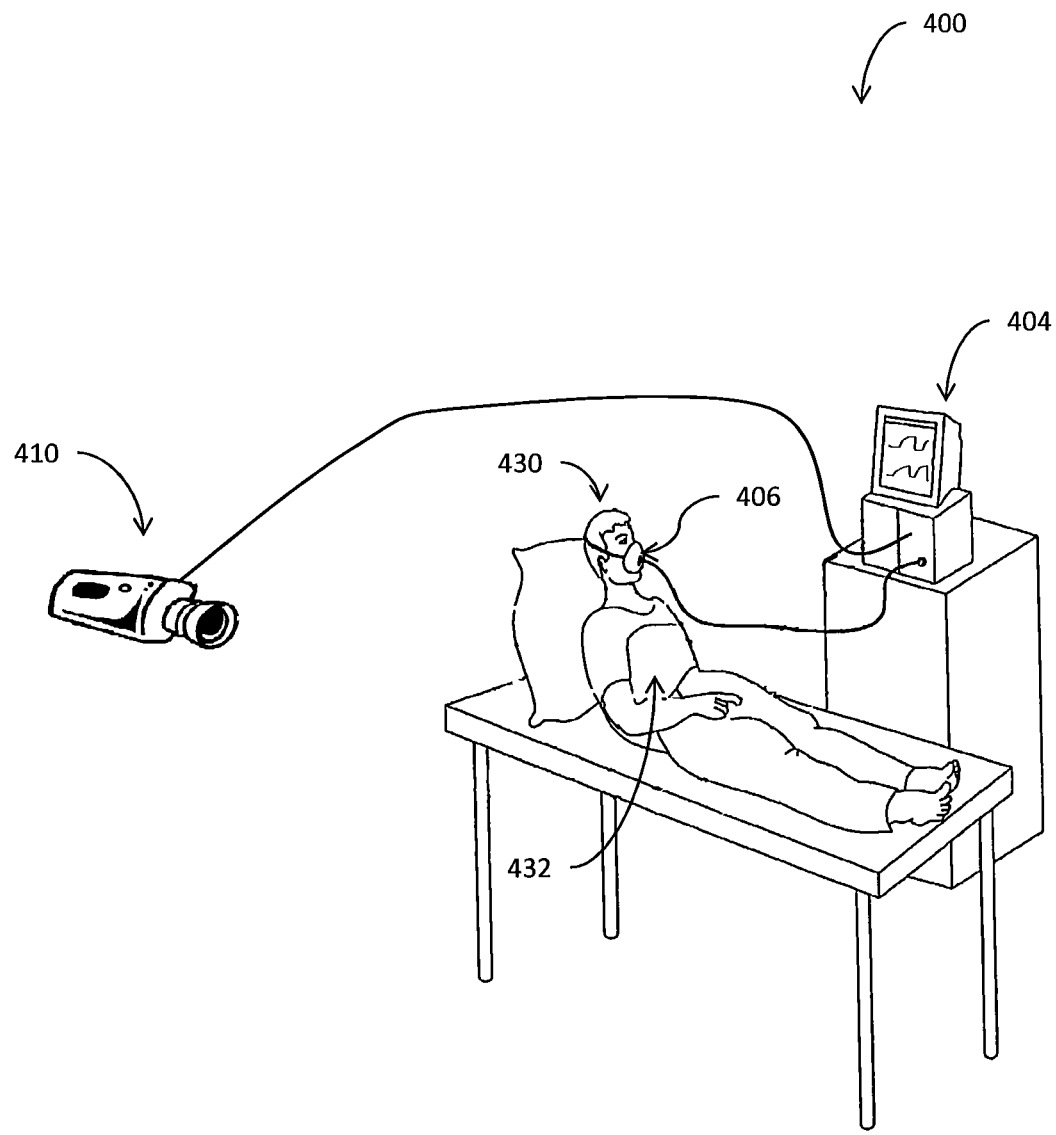
FIG. 4 schematically illustrates a capnography system with a camera breath tracking mechanism, according to some embodiments.

Reference is now made to FIG. 4, which schematically illustrates a capnography system 400 with a camera 410 breath tracking mechanism, according to some embodiments. According to some embodiments, camera 410 is configured to capture visual imagery of a torso 432 of a subject 430 such that movements of torso 432 would be identified and delivered to an analysis unit, such as computer 404. According to some embodiments, computer 404 is configured to obtain the visual imagery from camera 404 and to analyze movements of torso 432 and identify respiratory cycles and/or respiratory phases therefrom.

Additionally, computer 404 is further configured to obtain $CO_2$ samples or respiratory gas samples from a sampler, such as mask 406 or any consumable unit for obtaining respiratory gas samples, and to measure the respiratory $CO_2$ concentration within the gas using a $CO_2$ sensor (not shown).

According to some embodiments, computer 404 identifies baseline-phases from the respiratory cycles and/or respiratory phases, and associates $CO_2$ measurements to these phases to create baseline $CO_2$ measurements. According to some embodiments, computer 404 may establish a baseline value based on the baseline $CO_2$ measurements, and to modulate the respiratory $CO_2$ measurements according to the established baseline.

According to some embodiments, camera 410 may be configured to obtain infrared imagery of subject 430, or torso 432. According to some embodiments, camera 410 may be configured to provide motion (gradient) indications of various points in the field of view thereof. According to some embodiments, camera 404 may be configured to provide a "floating point" or "tracking point" or a selected or predetermined point on subject 430 or torso 432.

According to some embodiments, breathing/respiration of a user may result in movements in the torso area. According to some embodiments, the movements may include expansion and/or contraction of various areas of the torso, such as the chest area, thorax area, and/or the abdomen area. According to some embodiments, the movements may include elevation and withdrawal of the shoulder area.

Figure 5:
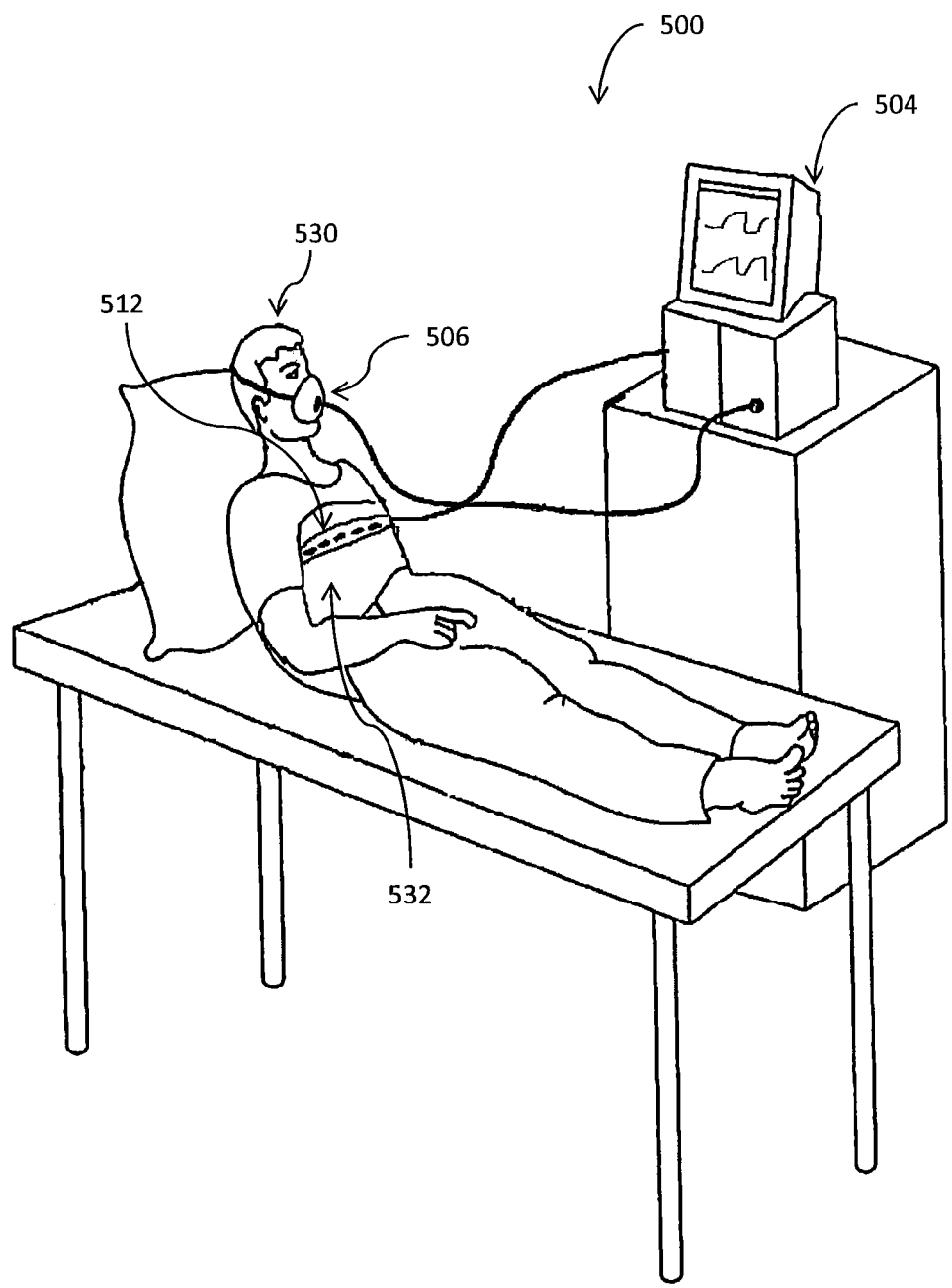
FIG. 5 schematically illustrates a capnography system with a torso-strap breath tracking mechanism, according to some embodiments.

Reference is now made to FIG. 5, which schematically illustrates a capnography system 500 with a torso-strap, such as chest-strap 512, breath tracking mechanism, according to some embodiments. According to some embodiments, chest-strap 512 is configured to measure the expansion and retraction at the chest area 532 of a subject 530. According to some embodiments, chest-strap 512 may provide signal(s) of indications and/or measurements related to the expansion and retraction to an analysis unit, such as controller 504. According to some embodiments, controller 504 is configured to analyze the signal(s) and to identify breath cycles or phases within the breath cycles based thereon. According to some embodiments, controller 504 may identify baseline-phases based on the signal(s) obtained from chest-strap 512.

According to some embodiments, controller 504 is further configured to obtain $CO_2$ samples or respiratory gas samples from a sampler, such as mask 506, and to measure the respiratory $CO_2$ concentration measurements within the gas using a $CO_2$ sensor (not shown). According to some embodiments, controller 504 identifies baseline-phases from the respiratory cycles and/or respiratory phases, and associates $CO_2$ measurements to these phases to create baseline $CO_2$ measurements. According to some embodiments, controller 504 may establish a baseline value based on the baseline $CO_2$ measurements, and to modulate the respiratory $CO_2$ measurements according to the established baseline.

Figure 6:
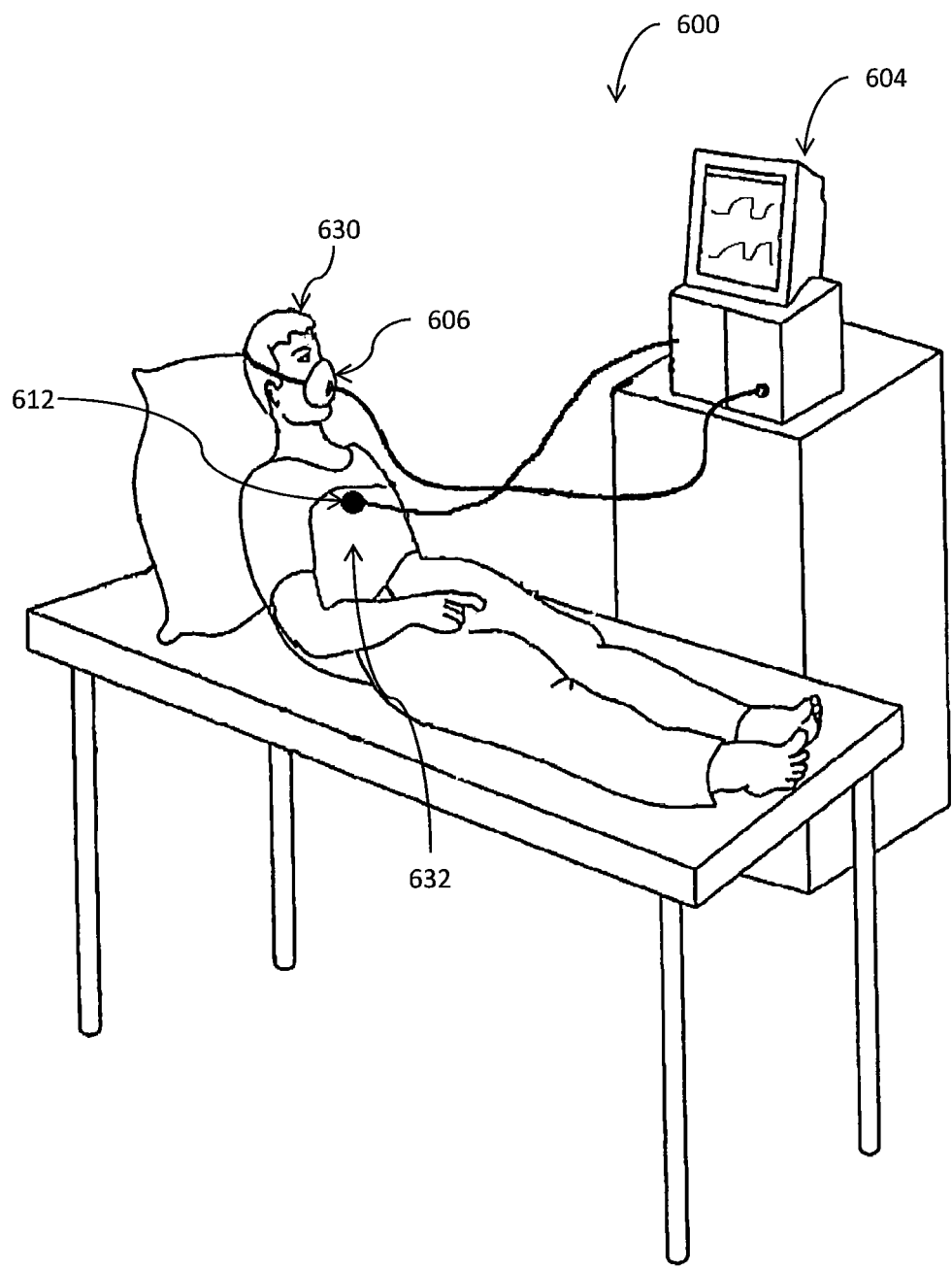
FIG. 6 schematically illustrates a capnography system with a motion sensor breath tracking mechanism, according to some embodiments.

Reference is now made to FIG. 6, which schematically illustrates a capnography system 600 with a motion sensor 612 breath tracking mechanism, according to some embodiments. According to some embodiments, motion sensor 612 is configured to measure the motion/movement of at least one spot at the chest area 632 of a subject 630. According to some embodiments, motion sensor 612 may provide signal(s) of indications and/or measurements related to the motion to an analysis unit, such as controller 604. According to some embodiments, controller 604 is configured to analyze the signal(s) and to identify breath cycles or phases within the breath cycles based thereon. According to some embodiments, controller 604 may identify baseline-phases based on the signal(s) obtained from motion sensor 612.

According to some embodiments, controller 604 is further configured to obtain $CO_2$ samples or respiratory gas samples from a sampler, such as mask 606, and to measure the respiratory $CO_2$ concentration measurements within the gas using a $CO_2$ sensor (not shown). According to some embodiments, controller 604 identifies baseline-phases from the respiratory cycles and/or respiratory phases, and associates $CO_2$ measurements to these phases to create baseline $CO_2$ measurements. According to some embodiments, controller 604 may establish a baseline value based on the baseline $CO_2$ measurements, and to modulate the respiratory $CO_2$ measurements according to the established baseline.

Figure 7:
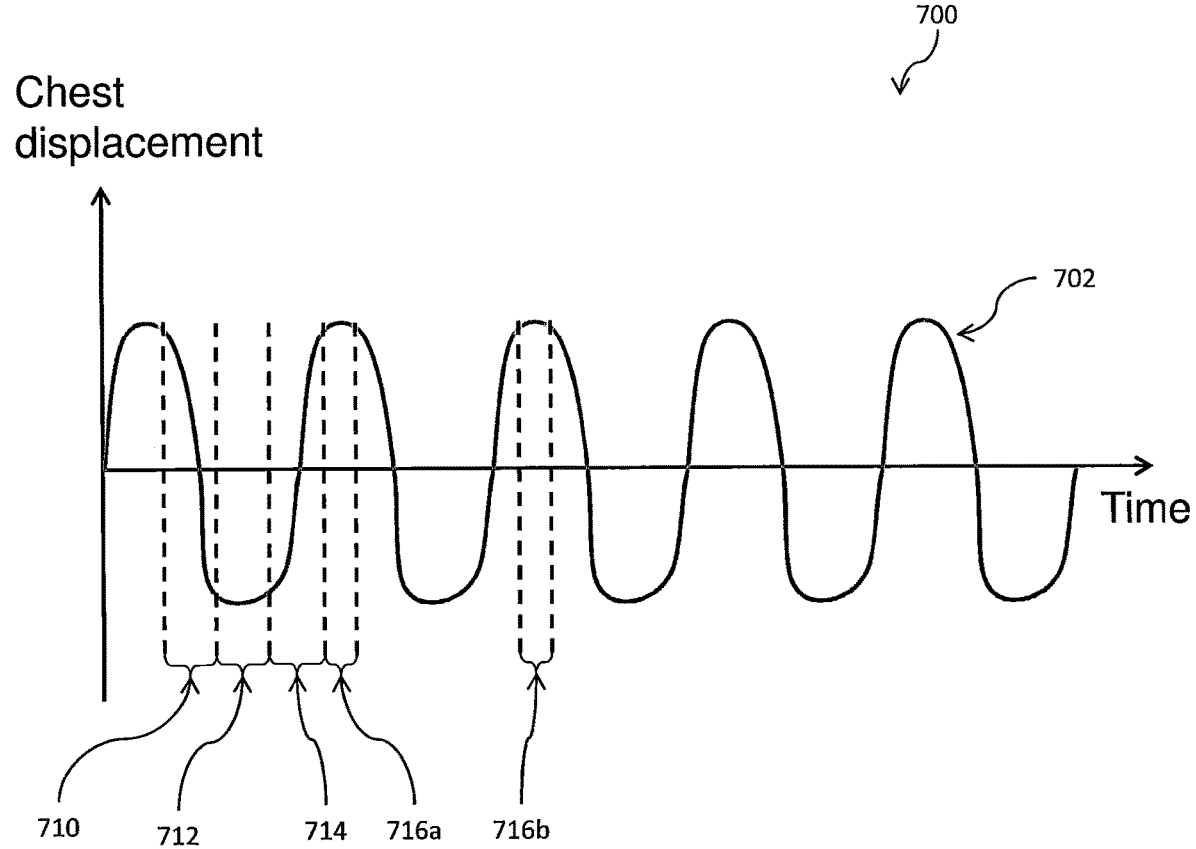
FIG. 7 schematically illustrates breath cycles and baseline-phases, according to some embodiments.

Reference is now made to FIG. 7, which schematically illustrates a graph 700 of breath cycles 702, according to some embodiments. As illustrated, the chest displacement varies over time and is indicative of various breath phases/stages. For example, according to some embodiments, various breath phases may be detected from the graph, such as an exhale phase 710, in which the chest is contracted, a vacant phase 712 wherein the respiratory gas has been exhausted out of the respiratory system and an inhalation has not begun yet, an inhale phase 714, in which air is sucked into the respiratory system and the chest is expanded, and hold phases (baseline-phases) 716a and 716b, in which the expansion is maximal and the exhale phases have not started yet.

Figure 8:
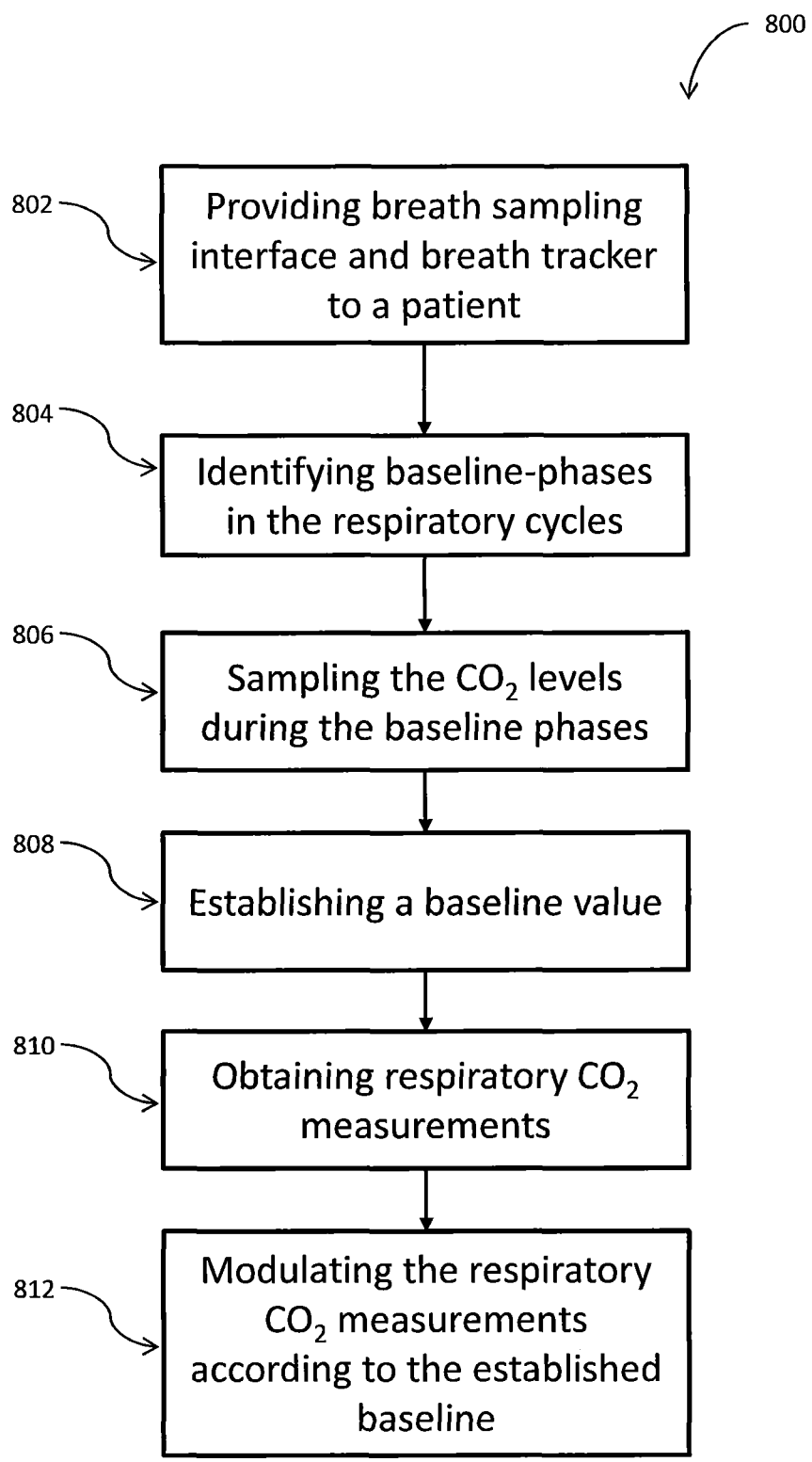
FIG. 8 schematically illustrates a flow chart of a method for capnography with baseline modulation, according to some embodiments.

Reference is now made to FIG. 8, which schematically illustrates a flow chart 800 of a method for capnography with baseline modulation, according to some embodiments. According to some embodiments, the method begins by providing a breath sampling interface to a patient, such as a sampling mask, and a breath/respiration tracker (step 802), then identifying baseline phases in the respiratory cycles of the patients based on information from the breath tracker (step 804), then (or concurrently/simultaneously) sampling the $CO_2$ levels during at least some baseline phases (step 806), then establishing a baseline value based on the $CO_2$ levels during the at least some baseline phases (step 808). Afterwards, according to some embodiments, the method proceeds with obtaining respiratory $CO_2$ measurements (step 810) and modulating the respiratory $CO_2$ measurements according to the established baseline (step 812).

According to some embodiments, modulating, altering, modifying and/or manipulating the respiratory $CO_2$ measurements may include subtracting/deducing the baseline value therefrom to obtain $CO_2$ levels. According to some embodiments, modulating, altering, modifying and/or manipulating the respiratory $CO_2$ measurements may include dividing the respiratory $CO_2$ measurements by the baseline value to obtain $CO_2$ levels.

Figure 9:
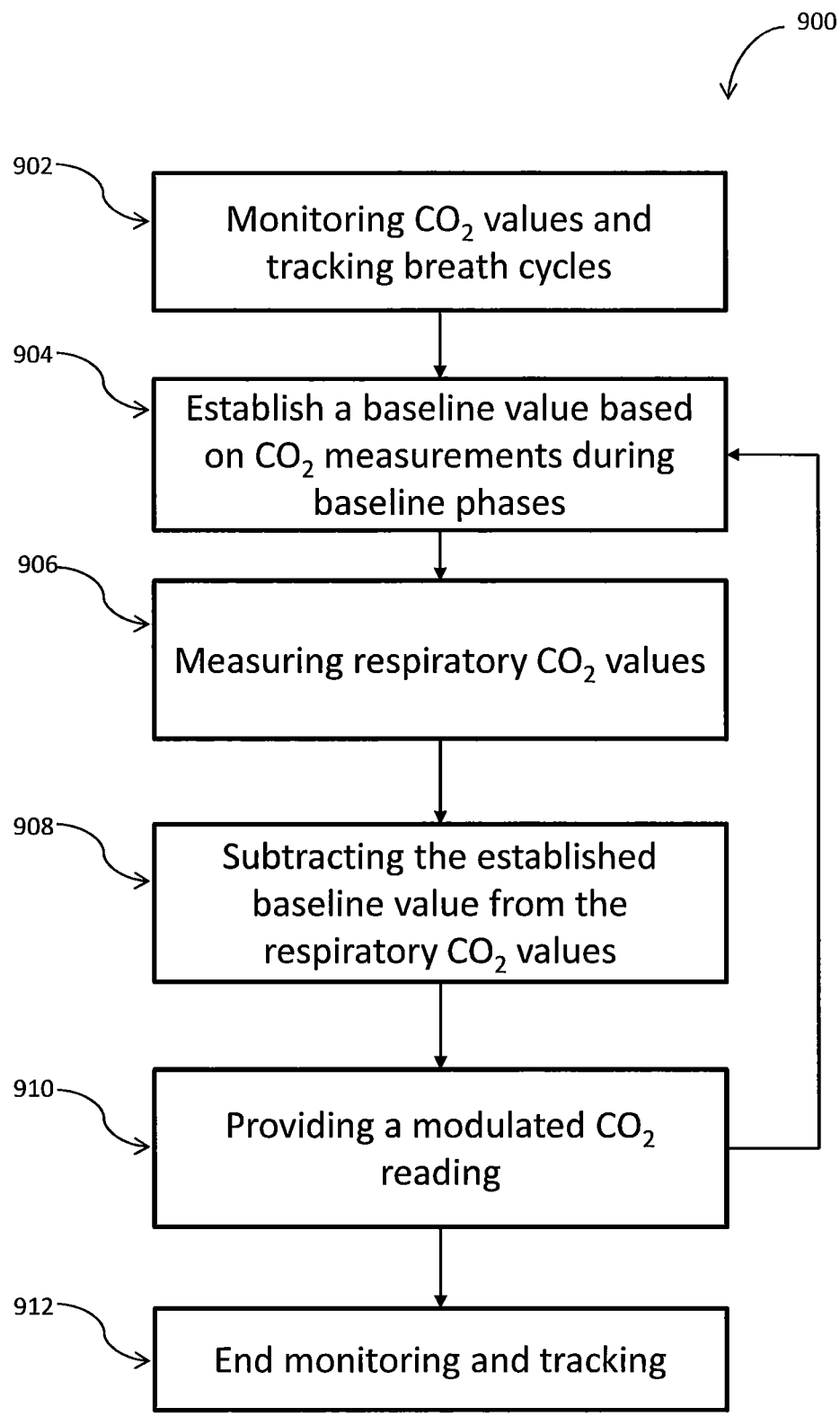
FIG. 9 schematically illustrates a flow chart of a method for capnography with recursive baseline modulation, according to some embodiments.

Reference is now made to FIG. 9, which schematically illustrates a flow chart 900 of a method for capnography with recursive baseline modulation, according to some embodiments. According to some embodiments, the method begins by monitoring $CO_2$ values of the respiration of a user, and tracking breath cycles thereof (step 902), then establishing a baseline value based on monitored $CO_2$ values during baseline phases (step 904), then measuring respiratory $CO_2$ values (step 906), subtracting the established baseline value from the measured respiratory $CO_2$ values (step 908) and providing a $CO_2$ levels (step 910) based on the subtraction.

According to some embodiments, the method may proceed by returning to step 904 for establishing a new baseline value, or ending the monitoring and tracking (step 912).

According to some embodiments, the respiratory $CO_2$ levels may be interpreted/derived from the respiratory $CO_2$ measurements by dividing it with $I_0$ (the baseline/zeroing level). For example, if $I_x$ refers to the intensity of IR radiation detected at the IR sensor, and $I_0$ is the baseline/zero level, then the respiratory $CO_2$ levels may be obtained by dividing as follows: respiratory $CO_2$ levels=$I_x/I_0$.

According to some embodiments, the IR sensors is configured to measure radiation/light intensities at an approximately 200 nm IR wavelength margin around a nominal 4.2 um point.

In comparison, in current capnography (utilizing two IR sensors) there may be three types of measured intensities:

$I_0$=the original intensity of the lamp (reference sensor)

$I_{x0}$=the intensity at CO2 zero level during inhalation (main sensor)

$I_x$=the intensity at non-zero level of CO2 during exhalation (main sensor)

The baseline is commonly derived from the portion $I_{x0}/I_0$, where $I_{x0}$ and $I_0$ are measured in parallel by main and reference sensor, correspondingly.

The $I_0$ value might change due to drifts and $I_x$ might be affected by the ambient air instant conditions, and this requires signal corrections/calibrations. Therefore, in case of utilizing two sensors in parallel, the reference signal ($I_0$) is constantly measured to provide quantifiable CO2 measurements, and advantageously when a single sensor is utilized it may be alternately measured using external tracking device.

As used herein, the terms "$CO_2$ levels" and "$CO_2$ values" are interchangeable and may relate to values/levels indicative of $CO_2$ concentration in a gas, and may be derived by manipulating/altering $CO_2$ measurements obtained from a $CO_2$ sensor.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising,"

when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A capnography device, comprising:
a respiratory-tracking system, configured to provide a tracking-signal indicative of baseline-phases within respiratory cycles, wherein the baseline-phases are confined between an end of inhalation and a start of exhalation;
a carbon dioxide ($CO_2$) sensor having an absorption chamber, an IR source, and an IR sensor;
wherein the absorption chamber is configured to provide respiratory $CO_2$ measurements of a subject's exhaled respiratory gasses within the absorption chamber and is filled with ambient air during the baseline-phase;
wherein the IR source is configured to provide IR radiation through the subject's exhaled respiratory gasses within the absorption chamber to the IR sensor;
wherein the IR source is configured, along with a detector, for detecting IR intensities of radiation irradiated from the IR source and passed through the exhaled respiratory gases within the absorption chamber; and
a processing system that is communicatively coupled to the respiratory-tracking system and the $CO_2$ sensor, for receiving the respiratory $CO_2$ measurements from the $CO_2$ sensor and, in real time and without a need for measuring and compensating for drifts between plural $CO_2$ sensors:
determining the baseline-phases from the tracking-signal derived by the processing circuitry, wherein the baseline-phases comprise baseline $CO_2$ measurements performed when the absorption chamber is filled with ambient air during a hold phase associated with null gas flow, and wherein the baseline $CO_2$ measurements are indicative of ambient $CO_2$;
distinguishing the baseline $CO_2$ measurements from the respiratory $CO_2$ measurements by use of the processing circuitry, and
determining a $CO_2$ value derived by the processing circuitry based on the baseline $CO_2$ measurements and the respiratory $CO_2$ measurements.

2. The device of claim 1, wherein the processing circuitry is configured to derive the $CO_2$ value by factoring the respiratory $CO_2$ measurements with the baseline $CO_2$ measurements.

3. The device of claim 1, wherein the processing circuitry is configured to derive the $CO_2$ value based on the baseline $CO_2$ measurements and the respiratory $CO_2$ measurements by:
establishing a baseline level from the baseline $CO_2$ measurements; and
dividing the respiratory $CO_2$ measurements by the baseline level, thereby deriving the $CO_2$ value.

4. The device of claim 1, wherein the respiratory-tracking system is configured to obtain a signal from the $CO_2$ sensor and detect various respiratory phases based on changes in the obtained signal.

5. The device of claim 1, wherein the respiratory-tracking system comprises a heart rate sensor.

6. The device of claim 1, wherein the respiratory-tracking system comprises a chest displacement tracking system configured to provide a signal indicative of displacement in the chest of the subject.

7. The device of claim 6, wherein the chest displacement tracking system comprises a belt configured to be placed on or wrap around a chest of the subject and provide chest displacement tracking by measuring the expansion and contraction of the chest.

8. A method for monitoring carbon dioxide ($CO_2$) in exhaled respiratory gasses of a subject, the method comprising:
obtaining a tracking-signal, wherein the tracking-signal is indicative of respiration-phases within a respiratory cycle;
identifying, via processing circuitry, a baseline-phase based on the tracking-signal, wherein the baseline-phase comprises baseline $CO_2$ measurements associated with ambient $CO_2$;
obtaining, via a $CO_2$ sensor having an absorption chamber, an IR source, and an IR sensor, respiratory $CO_2$ measurements of the subject within the absorption chamber, wherein the respiratory $CO_2$ measurements comprise a concentration of $CO_2$ in the exhaled respiratory gasses;
wherein the absorption chamber is filled with ambient air during the baseline-phase;
wherein the IR source is configured to provide IR radiation through the subject's exhaled respiratory gases within the absorption chamber to the IR sensor;
wherein the IR source is configured, along with a detector, for detecting IR intensities of radiation irradiated from the IR source and passed through the exhaled respiratory gasses within the absorption chamber;
and, in real time and without a need for measuring and compensating for drifts between plural $CO_2$ sensors:
distinguishing, via the processing circuitry, the baseline $CO_2$ measurements that are performed when the absorption chamber is filled with ambient air during a hold phase associated with null gas flow from the respiratory $CO_2$ measurements, based on the identified baseline-phase; and
determining, via the processing circuitry, respiratory $CO_2$ values based on the distinguished baseline $CO_2$ measurements and the respiratory $CO_2$ measurements, thereby, forming a capnogram.

9. The method of claim 8, wherein determining the respiratory $CO_2$ values based on the distinguished baseline $CO_2$ measurements and the respiratory $CO_2$ measurements comprises establishing a baseline level from the baseline $CO_2$ measurements.

10. The method of claim 9, wherein determining the respiratory $CO_2$ values based on the distinguished baseline $CO_2$ measurements and the respiratory $CO_2$ measurements further comprises subtracting the baseline level from the respiratory $CO_2$ measurements, thereby determining the respiratory $CO_2$ values.

11. The method of claim 8, wherein obtaining the tracking-signal indicative of respiration-phases within the respiratory cycle comprises obtaining the tracking-signal from a respiratory-tracking system.

12. The method of claim 11, wherein the respiratory-tracking system comprises a chest movement-tracking device.

13. The method of claim 12, wherein the chest movement-tracking device comprises a belt or strap configured to be placed on or around the chest or torso of the subject and to measure the expansion and contraction thereof.

14. The method of claim 8, wherein the baseline-phase is a phase in the respiratory cycle that is confined between the end of inhalation and start of exhalation, and in which the respiratory gas flow is idle.

* * * * *